United States Patent [19]

Meek et al.

[11] Plant 4,544

[45] Jun. 10, 1980

[54] CHRYSANTHEMUM PLANT CULTIVAR NAME: STRIPES

[75] Inventors: Jack M. Meek; William E. Duffett, both of Salinas, Calif.

[73] Assignee: Yoder Brothers, Inc., Barberton, Ohio

[21] Appl. No.: 10,856

[22] Filed: Feb. 9, 1979

[51] Int. Cl.[2] ..... A01H 5/00

[52] U.S. Cl. ..... Plt./74

[58] Field of Search ..... Plt./74

*Primary Examiner*—Robert E. Bagwill

*Attorney, Agent, or Firm*—Donald D. Jeffery

[57] ABSTRACT

A chrysanthemum plant known by the cultivar name Stripes and particularly characterized as to uniqueness by the combined characteristics of flat capitulum form; spooned daisy capitulum type; medium yellow ray floret color; diameter across face of capitulum ranging from 90 to 100 mm. at maturity; uniform seven week photoperiodic flowering response to short days; medium plant height when grown as a pinched spray pot; and semi-upright branching pattern.

8 Drawing Figures

The present invention comprises a new and distinct cultivar of *Chrysanthemum morifolium,* Ramat., hereinafter referred to by the cultivar name Stripes.

Stripes is a product of a planned breeding program which had the objective of creating new chrysanthemum cultivars with spooned daisy capitulum type, with yellow ray floret color, with seven or eight week flowering response, and with the ability to produce commercially acceptable quality in year round pot mum programs. Such traits in combination were not present in previously available commercial cultivars.

Stripes was originated from a cross made in a controlled breeding program in Barberton, Ohio in 1976. The female parent was #76047005 (unnamed seedling), a yellow spooned daisy originated from a cross between #75046011 (unnamed seedling) and #72018003 (unnamed seedling). The male parent of Stripes was #75179131 (unnamed seedling), a yellow spooned daisy originated from a cross between #73116030 (unnamed seedling) and #71388001 (unnamed seedling).

Stripes was discovered and selected as one flowering plant within the progeny of the stated cross by Jack M. Meek and William E. Duffett on May 12, 1977 in a controlled environment in Barberton, Ohio.

The first act of asexual reproduction of Stripes was accomplished when vegetative cuttings were taken from the initial selection in June, 1977 in a controlled environment in Barberton, Ohio, by a technician working under formulations established and supervised by Jack M. Meek and William E. Duffett. Continued asexual reproduction by vegetative cuttings for evaluative tests in flowering and stock programs in conjunction with horticultural examination of selected units initiated Feb. 3, 1978 has demonstrated that the combination of characteristics as herein disclosed for Stripes is firmly fixed and retained through successive generations of asexual reproduction.

Stripes has not been observed under all possible environmental conditions. The phenotype may vary significantly with variations in environment such as temperature, light intensity and daylength. The following observations, measurements, and comparisons describe plants grown in Salinas, Calif. under greenhouse conditions which approximate those generally used in commercial practice.

The following traits have been repeatedly observed and are determined to be basic characteristics of Stripes which in combination distinguish this chrysanthemum as a new and distinct cultivar:

(1) Flat capitulum form.

(2) Spooned daisy capitulum type.

(3) Medium yellow ray floret color.

(4) Yellow-green (immature) to yellow (mature) disc floret color.

(5) Diameter across face of capitulum ranging from 90 to 100 mm. at maturity.

(6) Uniform seven week photoperiodic flowering response to short days.

(7) Medium plant height (requiring 1–2 long day weeks prior to pinch and short days, and one application 2500 ppm B-9 SP 14 to 21 days after the beginning of short days to attain a flowered plant height of 30 to 45 cm.).

(8) Semi-upright branching pattern.

The accompanying photographic drawings show typical inflorescence and foliage characteristics of Stripes, with colors being as nearly true as possible with illustrations of this type.

Sheet 1 is a color photograph of the inflorescence of Stripes. Some degree of difficulty was encountered in obtaining accurate color representation of the ray floret color of Stripes, with the depicted color being more red (gold) or less yellow than the actual ray floret color. The color readings within the disclosure text are, however, correct. Sheet 2 is a black and white photograph showing three views of the inflorescence of Stripes. Sheet 3 is a black and white photograph showing the foliage of Stripes at three stages of growth. Sheet 4 is a black and white photographic comparison of the inflorescence of Stripes and the cultivar Spice, disclosed in U.S. Plant Pat. No. 3,777.

Of the many commercial cultivars known to the present inventors, the most similar in comparison to Stripes are Spice and Quills, disclosed in our pending application Ser. No. 903,034, filed May 4, 1978 (now U.S. Plant Pat. No. 4,401). Reference is made to attached Chart A which compares certain characteristics of Stripes to those same characteristics of Spice and Quills. General comparison are as follows:

In comparison to Spice, Stripes has lighter ray floret color, more upright branching pattern, larger diameter across face of inflorescence, and shorter flowering response period. The capitulum form, capitulum type, and plant height of Stripes are similar to those same characteristics of Spice. As seen on Sheet 4, the capitulum shape, despite being of similar form and type, has more pronounced flare at the tip of each ray floret.

In comparison to Quills, Stripes has different ray floret color. The capitulum form, capitulum type, branching pattern, plant height, and flowering response period of Stripes are similar to those same characteristics of Quills. The diameter across face of capitulum of Stripes shows less variation and is generally larger than that of Quills.

In the following description, color references are made to A Limit Color Cascade, by the Munsell Company, 1972 edition. The color values were determined between 10:30 and 11:00 A.M. on Nov. 16, 1978 under 100 foot-candle light intensity at Salinas, Calif.

Botanical classification: *Chrysanthemum morifolium,* Ramat., cv Stripes.

INFLORESCENCE

A. Capitulum: (See Sheets 1 and 2 of drawings):
- *Form.*—Flat.
- *Type.*—Spooned daisy.
- *Diameter across face.*—90 to 100 mm.

B. Corolla of ray florets:
- *Persistence.*—Resists shatter.
- *Color (general tonality).*—Medium yellow, 26-4.
- *Color (abaxial).*—25-5 to 26-5 (flair).
- *Color (adaxial).*—Ranging from 25-4 to 26-4 (immature) to 25-3 to 26-3 (mature).

C. Reproductive organs:
- *Androecium.*—Present disc florets only; scant to numerous; slight pollen.
- *Gynoecium.*—Present both ray and disc florets.

D. Corolla of disc florets:
- *Color.*—23-10 (immature) to 26-6 (mature).

PLANT

A. General appearance:
- *Branching pattern.*—Semi-upright.
- *Height.*—Medium.

B. Foliage (See Sheet 3):
- *Color (abaxial).*—Approximately 20-14.
- *Color (adaxial).*—Approximately 20-13 overlaid with white.

CHART A

COMPARISON OF STRIPES, SPICE, AND QUILLS.

| CULTIVAR | RAY FLORET COLOR | CAPITULUM FORM AND TYPE |
|---|---|---|
| Stripes | Medium Yellow | Flat spooned daisy |
| Spice | Dark Yellow | Flat spooned daisy |
| Quills | White | Flat spooned daisy |

| BRANCHING PATTERN | DIAMETER ACROSS FACE OF CAPITULUM | PLANT HEIGHT | FLOWERING RESPONSE PERIOD |
|---|---|---|---|
| Semi-upright | 90 to 100 mm. | Medium | 7 week |
| Semi-spreading | 75 to 80 mm. | Medium | 8 week |
| Semi-upright | 65 to 100 mm. | Medium | 7 week |

COMPARISONS MADE OF PLANTS GROWN AS PINCHED SPRAY POTS IN SALINAS, CALIFORNIA.

We claim:

1. A new and distinct cultivar of *Chrysanthemum morifolium,* Ramat., plant as shown and described, known by the cultivar name Stripes and particularly characterized as to uniqueness by the combined characteristics of flat capitulum form; spooned daisy capitulum type; medium yellow ray floret color; diameter across face of capitulum ranging from 90 to 100 mm. at maturity; uniform seven week photoperiodic flowering response to short days; medium plant height when grown as a pinched spray pot; and semi-upright branching pattern.

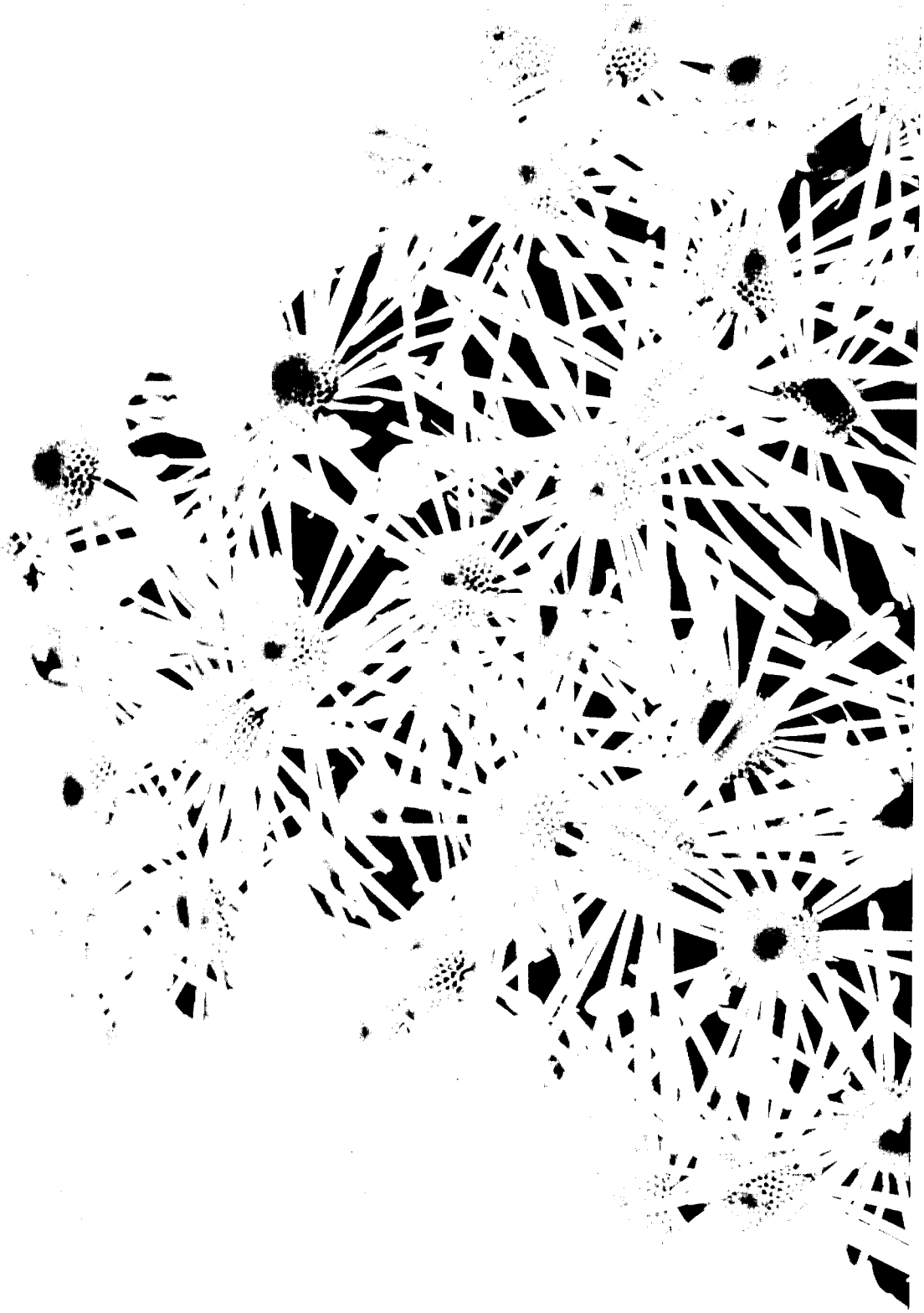

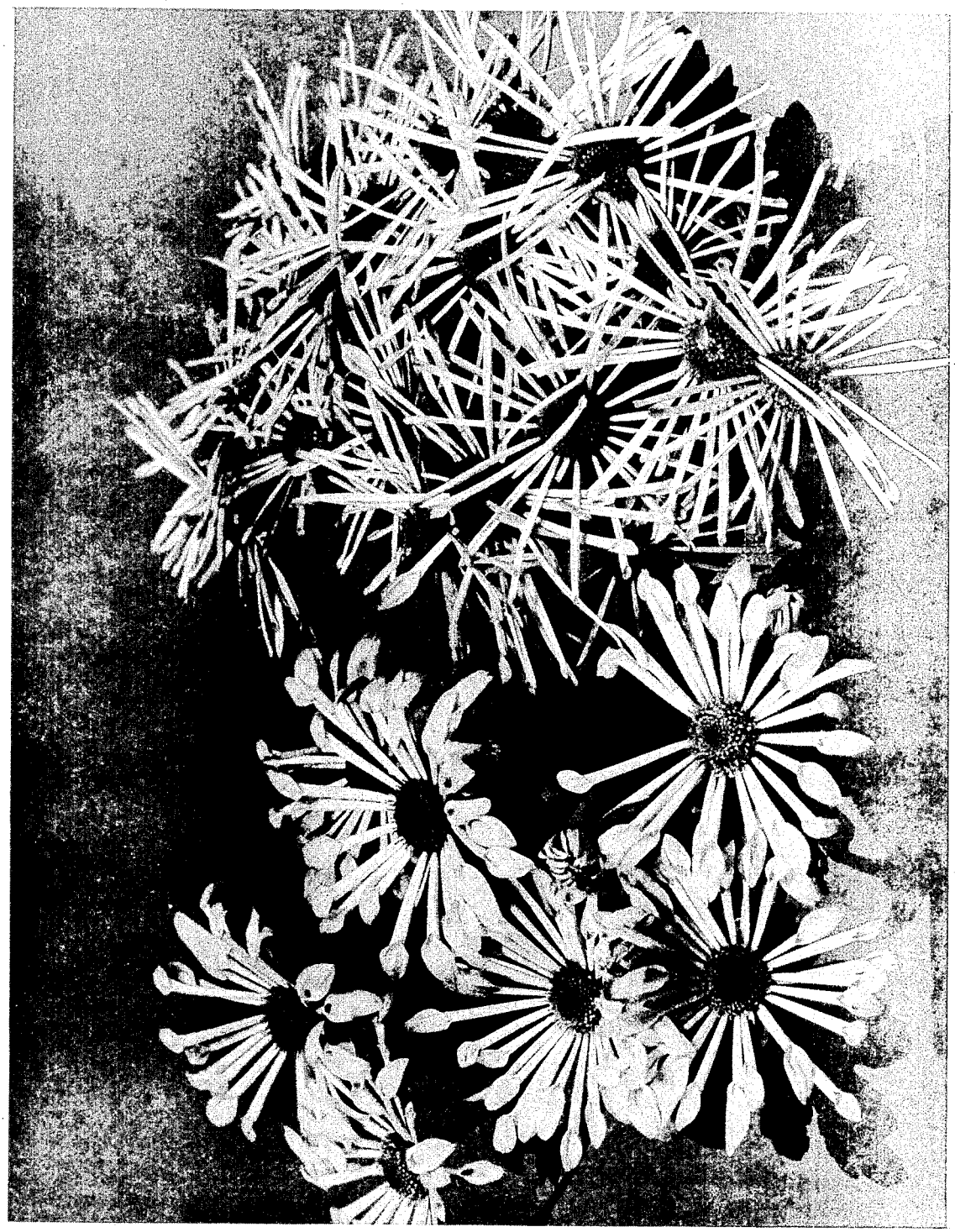

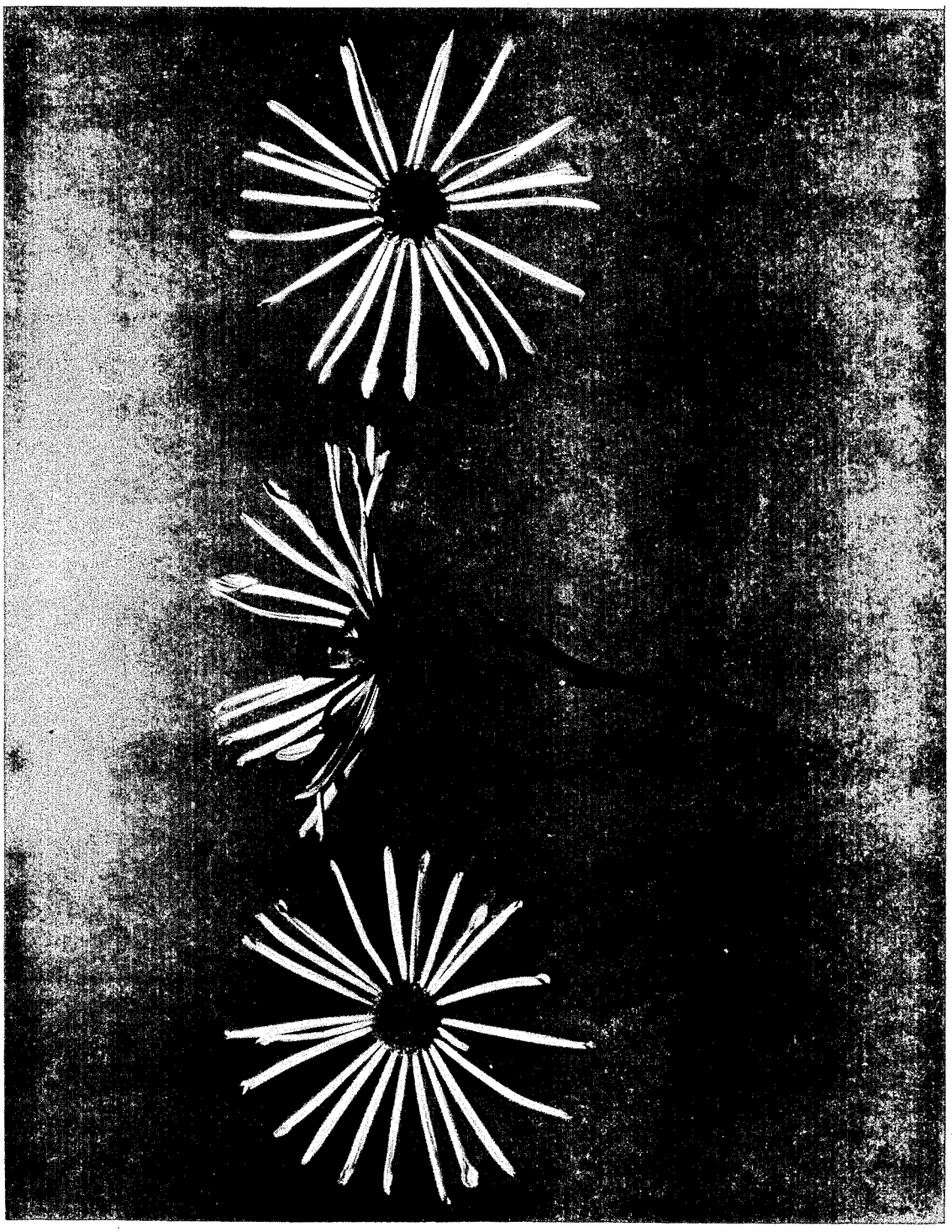

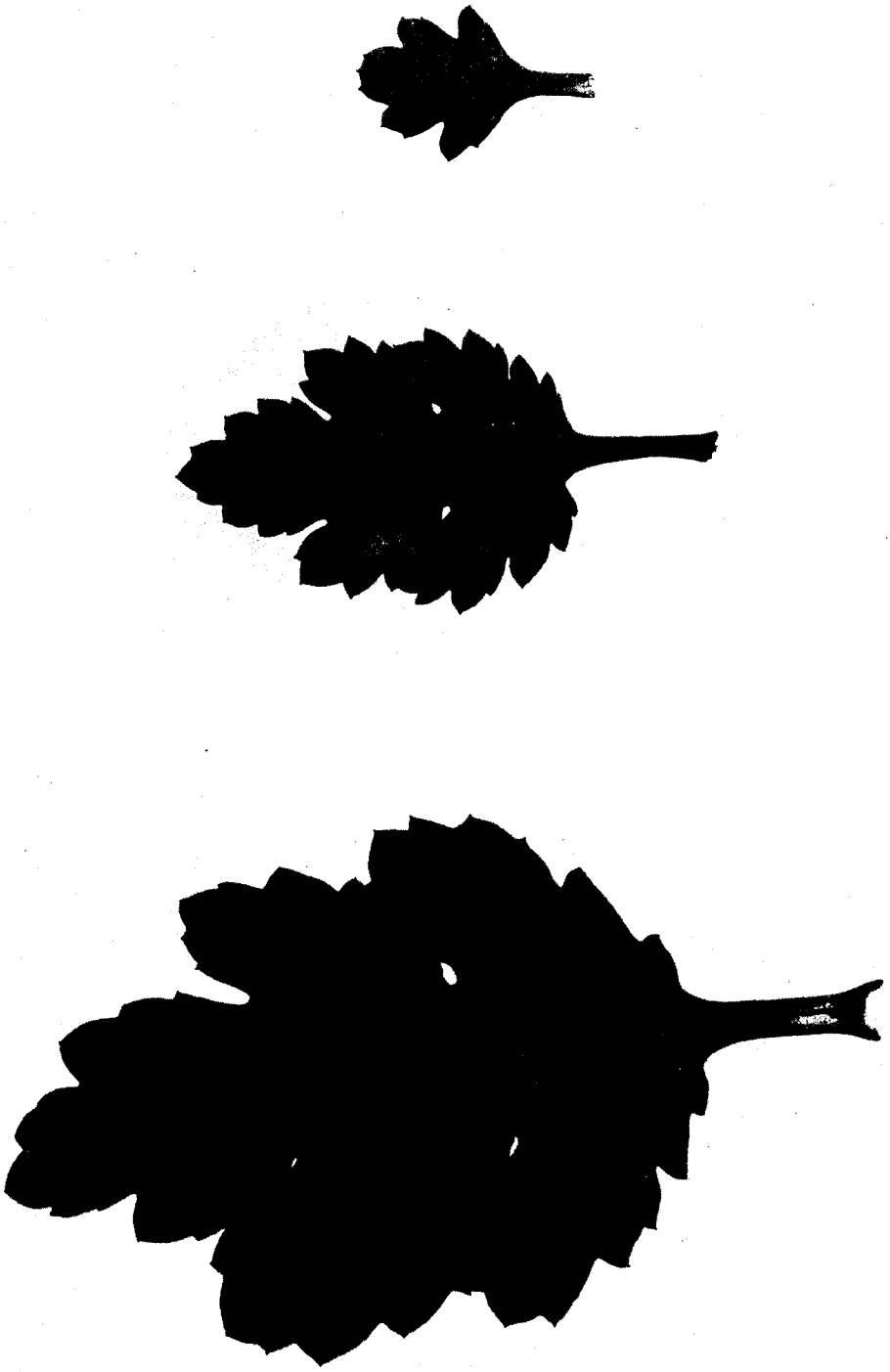

* * * * *